United States Patent
Fritzsche et al.

(10) Patent No.: US 7,263,445 B2
(45) Date of Patent: Aug. 28, 2007

(54) METHOD FOR THE SIMULTANEOUS DISSECTION IN SPECIFIC POSITIONS OF FILIFORM ORGANIC MOLECULAR CHAINS, IN PARTICULAR DNA

(75) Inventors: Wolfgang Fritzsche, Jena (DE); Karsten Koenig, Nerkewitzer Str. 18, Neuengoenna (DE) D-07778; Johann Michael Koehler, Golmsdorf (DE)

(73) Assignee: Karsten Koenig, Neuengoenna (DE)

( * ) Notice: Subject to any disclaimer, the term of this patent is extended or adjusted under 35 U.S.C. 154(b) by 494 days.

(21) Appl. No.: 10/450,544

(22) PCT Filed: Dec. 12, 2001

(86) PCT No.: PCT/EP01/14591

§ 371 (c)(1),
(2), (4) Date: Jul. 2, 2003

(87) PCT Pub. No.: WO02/48399

PCT Pub. Date: Jun. 20, 2002

(65) Prior Publication Data

US 2005/0026146 A1    Feb. 3, 2005

(30) Foreign Application Priority Data

Dec. 13, 2000  (DE)  ................. 100 62 532

(51) Int. Cl.
*B82B 3/00*   (2006.01)
*C12Q 1/68*   (2006.01)
(52) U.S. Cl. ................. 702/28; 435/6; 977/810
(58) Field of Classification Search ............... None
See application file for complete search history.

(56) References Cited

U.S. PATENT DOCUMENTS 5,714,328 A * 2/1998 Magda et al. ............... 435/6
6,027,890 A * 2/2000 Ness et al. ................. 435/6

FOREIGN PATENT DOCUMENTS

WO    WO98/51818    * 11/1998

OTHER PUBLICATIONS

Cut out or poke in—the key to the world of single genes: laser micromanipulation as a valuable tool on thelook-out for the origin of disease; 1997; Genetic Analysis Biomolecuar Engineering, by Krain Shuetze, Ingrid Becker, Karl-Friedrich et al., pp. 1-8.
The Film Nanoprocessing by Laser/STM Combination; 1994; A. A. Grobunov and W. Pompe; pp. 333-338.
Grobunov et al. Imaging and nanodissection of individual supercoiled plasmids by atomic force microscopy; 1992; Nucleic Acids Research, vol. 20, No. 3; pp. 445-447.

* cited by examiner

*Primary Examiner*—Marjorie A. Moran
(74) *Attorney, Agent, or Firm*—Jordan and Hamburg LLP

(57) ABSTRACT

The invention relates to a method for the simultaneous dissection in specific positions of filiform organic molecular chains, in particular DNA. The aim of the invention is to provided a method, by which a highly specific dissection can take place on certain sequences that can be freely selected and simultaneously on numerous filiform molecules. To achieve this, nanoparticles (1) are provided with a molecular chain (11) of any predeterminable sequence, which is selected to be complementary to a sequence of a molecule (2) that is to be dissected, said molecular chain(s) (11) is/are hybridised in the usual manner with the molecule, or specifically linked to said molecule in another manner and the nanoparticles (1) are subsequently subjected to a high-energy radiation of at least one wavelength, which can be absorbed by said nanoparticles (1).

13 Claims, 3 Drawing Sheets

Figure 1:
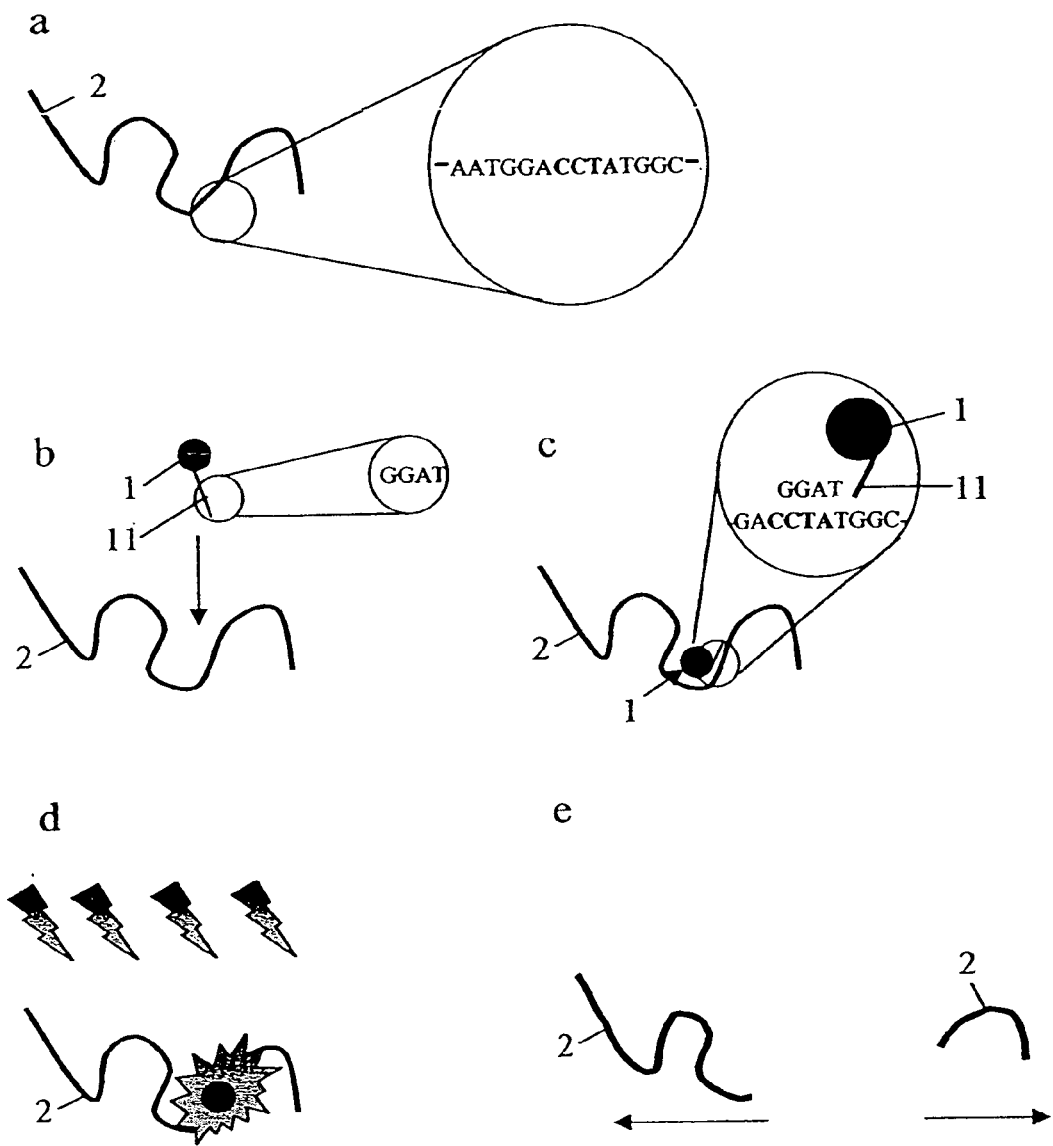

METHOD FOR THE SIMULTANEOUS DISSECTION IN SPECIFIC POSITIONS OF FILIFORM ORGANIC MOLECULAR CHAINS, IN PARTICULAR DNA

BACKGROUND OF THE INVENTION

The invention relates to a method for the simultaneous dissection in specific position of filiform organic molecular chains, in particular for the sequence-specific dissection of DNA. The dissection of DNA at predetermined positions is a fundamental technique of molecular biology. To date, in routine laboratory works only such enzymes are used (restriction enzymes) which have a specific dissection sequence. The enzyme EcoRI, for example, dissects double-stranded DNA at all positions with the following base sequence:

```
5' G A A T T C 3'
5' G A A T T C 3'
```

Such dissections are used in routine work for the manipulation of DNA, for example for the integration of new fragments or for a defined reduction. A complete field of DNA analytics, known as fingerprinting, is based on the variation of length distribution of DNA after the use of such enzymes, the length distribution is documented in the restriction fragment length polymorphism. If there is a mutation in the field of one dissection sequence in singular individuals (that is for example an A instead of a T in the scheme given above), the DNA cannot be dissected at this position, and DNA fragments develop which have other lengths than the ones in individuals without mutation at this position. Therefore, the pattern of the length distribution can be used for identifying the individual man. This fact is made use of for forensic purposes or for paternity affiliations. The extremely high sensitivity of this technique applied for this purposes (the change of an individual base can be detected) is also used for the determination of genetic defects (such as hereditary diseases) which are localized on the dissection sequences. When using all these techniques, however, one is restricted to the naturally existing enzymes and their dissection sequences, other positions cannot be dissected in this manner.

To avoid such restrictions single molecule based techniques have been developed for dissecting DNA at any positions by using a laser beam [Schütze, K., I. Becker, et al. (1997) "Cut out or poke in the key to the world of single genes: laser micromanipulation as a valuable tool on the look-out for the origin of disease" Genetic Analysis 14(1): 1-8] or by using the atomic force microscope [AFM, Henderson, E. (1992) "Imaging and nanodissection of individual supercoiled plasmids by atomic force microscopy" Nucleic Acids Research 20(3): 445-447]. These two methods have the significant disadvantage that they do not offer selectivity and are characterized by a large dissection width. Laser cutting destroys several hundreds of base pairs and generally an orientation can only be achieved on the basis of typology (start/end) or by means of a fluorescence-marked DNA fragment (FISH: fluorescence in situ hybridization), whereby the optic resolution (>100 . . . 200 nm) limits this method. In addition to this, both methods are single molecule based techniques and do only allow to dissect a single molecule instead of a number of molecules according to the lab standard. Thus, a characterization (for example gel-electrophoresis) or a further processing requires a multiplication in order to be compatible with the standard laboratory methods.

To avoid the limitation caused by the restricted spatial resolution of such physical methods, the proximity focusing technique has been used in material processing. This technique uses a small object (a scanning tip of an atomic focusing microscope having a radius in the lower nanometer range) as a high-intensive secondary light source which is supplied by radiated laser light [Gorbunov, A. A. and W. Pompe (1994) "Thin Film Nanoprocessing by Laser/STM Combination" phys. stat. sol. (a) 145: 333-338]. This secondary radiation becomes effective in the vicinity of the small object (near-field effect), and thus a focusing effect in the size of the object is achieved.

SUMMARY OF THE INVENTION

The aim of the invention is to provide a method by means of which a highly specific dissection can take place on certain sequences that can be freely selected and simultaneously on numerous filiform molecules, in particular DNA. This aim is achieved by a specific marking by means of nanoparticles which are subsequently subject to energy radiation. The invention is based on the principle that energy is sent into the sample in a broader beam, but due to an appropriately placed nanoobject it has only an influence on a small volume area. This effect is achieved by the nanolocal conversion of the radiation energy that is absorbed by the nanoobject into heat and by chemical conversion.

In fact, single molecules such as dyes can be positioned well in the nanorange, but their efficiency for local absorption and energy conversion is low. Moreover, due to the absorption of the radiation they often lose their absorbing effect very rapidly in photochemical processes. This invention, however, uses electron-conducting nanoparticles, metallic nanoparticles in particular, and here the ones from heavy precious metals especially. Unlike dye markers they can be used in a broad spectral range, too and are not limited to a small one. Apart from electromagnetic radiation (IR radiation, visible light, UV light, X-radiation), the energy of the radiation of high-speed particles such as electrons or ions can be effectively converted, too. In the field of optics, the efficiency of the radiation conversion is increased thanks to the narrow intensive bands of the plasma resonance. By working with particles which consist of the same material but have different dimensions, plasma resonance can be used for various wave lengths to address local cutting positions additionally or to obtain locally very limited dissections by the cooperative effect of two or more wave lengths.

DETAILED DESCRIPTION OF THE INVENTION

Figure 2:
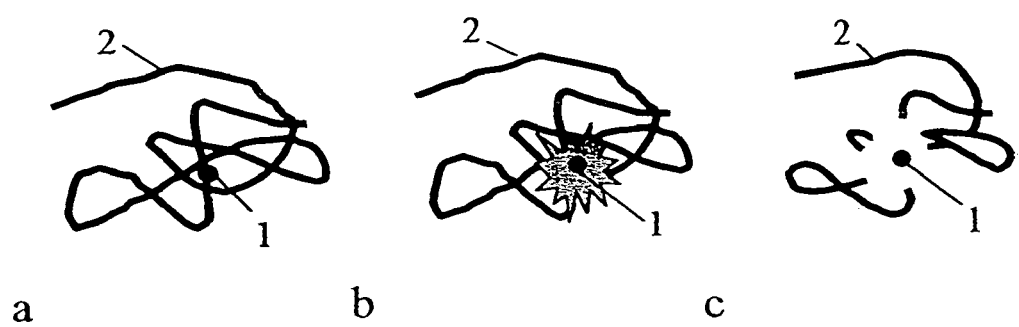
Figure 3:
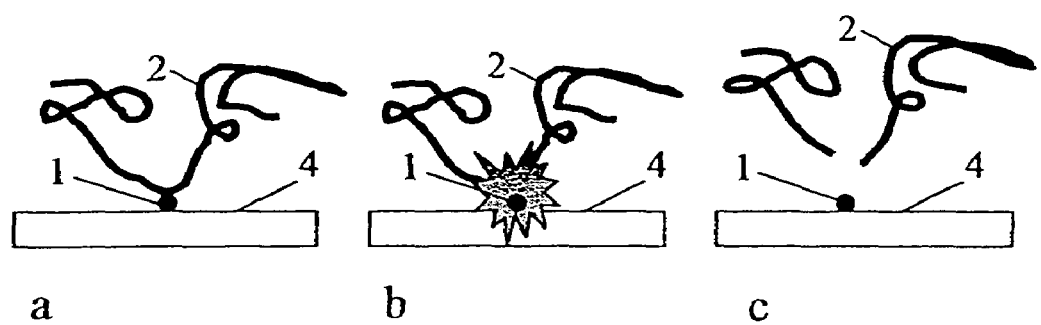

The present invention will now be described in more detail by way of the following schematic example. The figures show:

FIG. 1a-e the schematic flow of the process by using one single molecular strand, FIG. 2a-c demonstrates certain difficulties when dissecting long-stretched molecules which show a three-dimensional folding and FIG. 3a-c shows the possible solution for avoiding the difficulties according to FIG. 2a-c.

DESCRIPTION OF THE PREFERRED EMBODIMENTS

For the present invention nanoparticles in the range of between 1 nm and 150 nm are used. In the example, gold nanoparticles 1 having a typical diameter of 15 nm are placed along a DNA strand 2 by a specific linkage to the sequence desired and are then subject to the radiation of the appropriate kind of energy (light). For this purpose, the nanoparticles 1 are first provided with a short DNA molecule 11 with more than ten bases, whereby only four of them are shown in FIG. 1b and c to allow a clearer overview. The sequence of this molecule is complementary to the DNA 2 to be dissected (target DNA, see FIG. 1a, for which a part sequence of a single strand is given as example in enlarged presentation) at the dissection point. In this way, a specific link of the nanoparticle 1 at a defined place along the DNA 2 is achieved (see FIG. 1c, whereby the specific linkage is again shown in enlarged presentation). Afterwards, one, preferably more DNA-molecules specifically marked in such a way is/are subject to high-energy radiation, for example to the light of an argon laser at one or more wave lengths, to address different nanoparticles which are linked to various sequence fragments. Due to the energy absorption at the nanoparticle, the particle and the environment are heated up locally in the way demonstrated schematically in FIG. 1d. This heat causes the dissection of the DNA strand. (See FIG. 1e.) The precision of the dissection (=width of dissection) can be controlled finely by adjusting the radiated energy. A target precision (=location of dissection) in the lower nanorange is ensured by the self-organizing system of particles with any predeterminable DNA linking sequence, which link to the dissection area(s) on the target DNA by hybridization (copulation of complementary DNA fragments). This hybridization can take place for example after the local opening (melt open) of the DNA double-strand in form of a double-strand or by the addition of the linkage sequence to the double-strand by forming a triplex-structure (energetically favored under certain conditions depending on salt content and base frequency in particular). This invention has the considerable advantage that the energy can be radiated onto a larger area. From the technological point of view, it is therefore less complicated than the conventional methods.

For the long-stretched DNA molecules a problem is caused by their typically three-dimensional folding. As shown in FIG. 2a-c, some additional dissections can be produced unintentionally despite a precise positioning, because other parts of the molecule 2 come close to the nanoparticle excited 1 due to the back-folding of the strand. A certain control of the back-folding is possible via the salt concentration of the solution, because it influences the rigidity of DNA. A globular structure can be avoided by stretching the molecule 1, but it requires single molecule based techniques (optical tweezers) or other time-intensive methods such as liquid stream and/or electrical field preferentially combined with a unilateral binding.

A simple and highly parallelizable solution variant is given by the linkage of the nanoparticles 1 on suitable surfaces 4. For this purpose, the substrate material used has to offer such a quality that the absorption of the radiated energy is not considerable, for example glass if light is used to excite the nanoparticles. For the present invention the nanoparticles 1 are formed by spots structured on the surface 4. After the immobilization of the nanoparticles 1 with short DNA 11 on the surface 4, whereby, for example, in the case of using glass its surface can be coated with silane or provided with another coating allowing the adhesion of the particles, the DNA 2 settles according to the scheme of the specific linkage by DNA base coupling (hybridization) described in FIG. 1. Now, the DNA molecule 2 cannot surround the nanoparticle 1 in space any longer, because the back-folding chances are limited considerably. Thus, the probability of unintentional multi-dissections shown in FIG. 2 is minimized.

Advantageous applications of the recommended method are the following ones:

the restriction analysis of DNA (such as restriction fragment length polymorphism). By means of the procedure recommended these analyses can be performed for special genes in an optimally adjusted manner. A lot of genes being outside the known enzyme dissection areas can now be reached.

the deliberate cutting of gene fragments out of bigger DNA molecules. For this purpose, the cutting sequences can be selected in such a way that the searched fragment can be simply isolated (for example by a unique length) and has not to be separated from a number of DNA fragments which have the same or a comparable length.

the controlled release of DNA fragments. For this purpose, a procedure is known according to the prior state of technology in which surface areas with double-stranded DNA are heated up by laser energy to such an extent that the double-strand will be opened (melt open). In this method, temperatures above the melting point (50-95° C.) are to be generated locally without reaching temperature peaks which damage the molecules. Based on the invention recommended this complicated temperature regime can be replaced by the use of immobilized colloids which link the molecules with the dissection sequence. (See FIG. 3a.) These molecules are dissected by a special exposure (FIG. 3b) and the fragments are released (FIG. 3c). Moreover, this procedure can be parallelized by linking several dissection sequences in various surface areas which are than subject to light independently from each other. In this way, the appropriate fragments are released as defined.

The invention is not limited to the sequence specific dissection of DNA described in the examples, but it can also be used for other biopolymers which allow a position-specific linkage of the nanoparticles provided with suited linking partners. Moreover, the kind of radiation used can differ from the one described here, as far as the nanoparticles used absorb the energy radiated.

The nanoparticles can be formed by metal and semiconductor particles or by composites of these materials and they can include organic components. The diameter of the particles can be adjusted by a separation procedure, for example by separating metal, semiconductor or organic materials.

The use of different dimensional classes of particles in combination with appropriately adjusted sources of radiation allows the independent processing of various subset. By using different particle classes, two in this example, which differ from each other in their energy absorption (i.e., caused by their different diameters), it is possible to activate only one class deliberately by selective radiation.

The invention claimed is:

1. Method for dissection in specific positions of one or more nucleic acid molecular chains, comprising providing GOLD nanoparticles with molecular chains, wherein the molecular chains are complementary to sequences of the nucleic acid molecular chains that are to be dissected;

linking the provided molecular chains complementarily to respective said nucleic acid molecular chains; and subsequently dissecting said one or more nucleic acid molecular chains by subjecting the nanoparticles to high-energy radiation of at least one wavelength which is absorbed by said nanoparticles.

2. Method according to claim 1, wherein each of said nanoparticles comprises a plurality of gold atoms.

3. Method according to claim 1, wherein said nanoparticles have a size in the range of 1 mm to 150 nm.

4. Method according to claim 1, wherein the nucleic acid molecular chains comprise DNA.

5. Method according to claim 4, wherein the linking comprises hybridization of the molecular chains of said nanoparticles with the nucleic acid molecular chains.

6. Method according to claim 1, wherein the dissecting is effected by heating of the nanoparticles, said heating resulting from the subjecting of the nanoparticles to the high-energy radiation.

7. Method according to claim 1, wherein
the nanoparticles are of at least two different high-energy radiation absorption characteristics, and
nanoparticles of a particular high-energy radiation absorption characteristic have molecular chains of identical sequences.

8. Method according to claim 7, wherein
the nanoparticles of at least two different high-energy radiation absorption characteristics comprise at least some nanoparticles of identical composition, and
said nanoparticles having different high-energy radiation absorption characteristics and identical composition are of different sizes.

9. Method according to claim 1, wherein the high-energy radiation comprises diffusely radiated high-energy light.

10. Method according to claim 1, wherein the nanoparticles are of at least two different compositions, wherein nanoparticles of identical composition have molecular chains of identical sequences.

11. Method according to claim 1, wherein the nanoparticles provided with the molecular chains are immobilized unilaterally on at least one surface.

12. Method according to claim 11, wherein said at least one surface comprises a material which absorbs substantially less of said high-energy radiation than is absorbed by said nanoparticles or absorbs none of said high-energy radiation.

13. Method according claim 11 or 12. wherein the nanoparticles comprise spots on the surface.

* * * * *